(12) United States Patent
Friedman et al.

(10) Patent No.: US 6,235,473 B1
(45) Date of Patent: May 22, 2001

(54) GENE PEN DEVICES FOR ARRAY PRINTING

(75) Inventors: Mitchell Friedman, Baltimore; Yu-Hui Rogers, Damascus; Michael Boyce-Jacino, Finksburg, all of MD (US)

(73) Assignee: Orchid BioSciences, Inc., Princeton, NJ (US)

( * ) Notice: Subject to any disclaimer, the term of this patent is extended or adjusted under 35 U.S.C. 154(b) by 0 days.

(21) Appl. No.: 09/109,915

(22) Filed: Jul. 2, 1998

(51) Int. Cl.[7] .............................. C12Q 1/68; C07H 21/04; B01J 19/00; B32B 5/02; G05B 17/00
(52) U.S. Cl. ........................ 435/6; 435/286.4; 536/23.1; 536/24.31; 536/24.32; 422/13 D; 422/131; 422/116
(58) Field of Search .................... 435/6, 286.4; 422/131, 422/130, 116

(56) References Cited

U.S. PATENT DOCUMENTS

| | | |
|---|---|---|
| 4,216,245 | 8/1980 | Johnson . |
| 4,877,745 | 10/1989 | Hayes et al. . |
| 5,139,812 | 8/1992 | Lebacq . |
| 5,143,854 | 9/1992 | Pirrung et al. . |
| 5,412,087 | 5/1995 | McGall et al. . |
| 5,445,934 | 8/1995 | Fodor et al. . |
| 5,474,796 | 12/1995 | Brennan . |
| 5,508,200 | 4/1996 | Tiffany et al. . |
| 5,510,270 | 4/1996 | Fodor et al. . |
| 5,551,487 | 9/1996 | Gordon et al. . |
| 5,554,339 | 9/1996 | Cozzette et al. . |
| 5,624,711 | 4/1997 | Sundberg et al. . |
| 5,731,152 | 3/1998 | Maracas et al. . |
| 5,733,509 | 3/1998 | Ackley et al. . |
| 5,741,700 | 4/1998 | Ershov et al. . |
| 5,756,050 | 5/1998 | Ershow et al. . |
| 5,759,779 | 6/1998 | Dehlinger . |
| 5,865,224 | * 2/1999 | Ally et al. . |
| 6,001,311 | * 12/1999 | Brennan . |

FOREIGN PATENT DOCUMENTS

| | | |
|---|---|---|
| 0728520 | 8/1996 | (EP) . |
| 9511995 | 5/1995 | (WO) . |
| 9727329 | 7/1997 | (WO) . |
| 9814770 | 4/1998 | (WO) . |
| 9816830 | 4/1998 | (WO) . |
| 9829736 | 7/1998 | (WO) . |
| 9939829 | 8/1999 | (WO) . |

OTHER PUBLICATIONS

Schena, M., "Genome analysis with gene expression microarrays," *BioEssays* 18:427–431 (1996).
Schena, et al., "Parallel human genome analysis: Microarray–based expression monitoring of 1000 genes," *PNAS USA* 93:10614–10619 (1996).
Pastinen, et al., "Minisequencing: A Specific Tool for DNA Analysis and Diagnostics on Oligonucleotide Arrays," *Genome Research* 7:606–614 (1997).

* cited by examiner

*Primary Examiner*—Kenneth R. Horlick
*Assistant Examiner*—Jeffrey Siew
(74) *Attorney, Agent, or Firm*—David A. Kalow; Kalow & Springut LLP (57) ABSTRACT

The invention concerns an apparatus for printing arrays of molecules and methods for printing these arrays. More particularly, the invention relates to a gene pen apparatus that may be used for delivering arrays of oligonucleotides on solid supports from a multiplicity of reagent reservoirs through flow controlling means. The flow controlling means may for example, be either a pin valve means or a wicking means.

43 Claims, 6 Drawing Sheets

GENE PEN DEVICES FOR ARRAY PRINTING

FIELD OF THE INVENTION

The present invention relates generally to methods and devices for immobilizing molecules on array supports.

BACKGROUND OF THE INVENTION

The immobilization of test molecules on array supports has had a significant impact on drug discovery and medical diagnostic methods. The basic approaches for generating arrays of test molecules such as nucleic acid, protein or other organic molecules fall into two general categories. In the first such approach the test molecules are directly synthesized onto the array support, while in the second such approach the test molecules are attached to the support post-synthetically. Each approach has its own limitations and drawbacks. For example, when an array is created by direct synthesis onto an array support, the efficiency of each synthetic step affects the quality and integrity of molecules forming the array. The magnitude of the problem increases with the complexity of the individual molecules, potentially resulting in an undesirable percentage of incorrectly synthesized molecules and incomplete sequences. Such contaminants can interfere with subsequent use of the array. In contrast, the second approach to array production allows the desired molecules to be synthesized and purified by conventional methods prior to their formation into an array. Consequently, the quality of the arrayed molecules, and thus the quality of the resultant array, is potentially greater than that produced by the direct synthesis approach. However, a simple, effective patterning device for the preparation of arrays from pre-synthesized molecules is currently lacking.

The major challenges in constructing arrays of intermediate to high complexity (and/or density) include reagent/liquid confinement, volume control, position registration, the limited number of different array positions that can be simultaneously applied (parallelism), and speed. Several approaches to array production have been attempted with varying degrees of success.

Simple arrays have been constructed by manually pipetting a small amount of each desired test reagent onto a support, gradually building up an array. The limitations to such an approach are obvious. It is slow, few test reagent can be applied simultaneously, and position registration and spacing are poor. For example, Pastinen et al. (Genome Research, 7:606–614 (1997)) create an array of oligonucleotides by manually applying 0.5 $\mu$L of a solution of 5'-amino-modified oligonucleotides onto an epoxide-activated glass slide to produce a 3×3 array of oligonucleotides on a 0.36 $cm^2$ area of a preprinted glass slide.

Other, more traditional printing methods have been used to create patterns of a few different reagents on a solid support. Means such as silk screening, offset printing, and rotogravure printing have been used in the production of reagent test strips. In such methods, each reagent ink is applied separately. Thus, the number of different reagents that may be applied is limited. Furthermore, there is considerable potential for position registration difficulties. Johnson, for example, (U.S. Pat. No. 4,216,245) discusses methods for the production of reagent test strip devices.

Pipette dispensing of reagents can be automated. Automation potentially increases the speed and accuracy of array production, while decreasing the necessary spacing between array positions. However, the utility of automated pipetting methods are severely limited in the number of different reagents that may be simultaneously applied (low parallelism), and by the potential for aerosol formation from air bubbles. Since the array is built by the sequential addition of different reagents, producing a complex array is time consuming. Cozzette et al., for example, (U.S. Pat. No. 5,554,339) discusses the use of microsyringes for dispensing reagents during the production of biosensor devices.

High-speed robotics have also been used to print microarrays of amino-modified cDNA molecules onto silylated glass microscope slides (CEL Associates, Houston) or poly-1-lysine coated microscope slides (Schena, Bioassays, 18:427–431 (1996); Schena et al., Proc. Natl. Acad. Sci., U.S.A., 93:10614–10619 (1996).

Another approach to array printing is an adaptation of ink-jetting technology. For example, Hayes et al. (U.S. Pat. No. 4,877,745) discusses an ink-jet type method and apparatus for dispensing reagents, particularly in the production of reagent test strips.

Pin transfer is one approach that allows the simultaneous transfer of greater numbers of samples than possible with the above approaches Pirrung et al., U.S. Pat. No. 5,143,854, Fodor et al., U.S. Pat. No. 5,510,270, Fodor et al., U.S. Pat. No. 5,445,934, and Chee et al., WO 95/11995) discuss the production of high density oligonucleotide arrays through a photolithographic synthesis of the oligonucleotides directly onto a derivatized glass substrate.

McGall et al. (U.S. Pat. No. 5,412,087) discusses a method for the production of a high density oligonucleotide array from pre-synthesized oligonucleotides.

Lebacq (U.S. Pat. No. 5,139,812) discusses the use of a pen, containing ink comprising a solution of a target nucleic acid, for cryptographically marking and thereby protecting valuable objects, such as art.

Despite all such methods, a method or apparatus capable of applying multiple "inks", containing different species of organic molecules, thereby creating an array, would be desirable. The present invention provides improved devices and methods for the production of arrays of molecules on solid or semi-solid supports. Previously, arrays could be constructed either manually, which is both time consuming and imprecise, or mechanically through the use of photolithographic, robotically-controlled or otherwise complex apparatus for the precise metering and placement of molecules. Alternatively, arrays could be constructed through direct chemical synthesis on a solid support. Such devices and methods have required undesirable tradeoffs between purity of the molecules forming the array, reagent confinement, volume control, position registration, parallelism, and speed. The present invention addresses the drawbacks of previous devices and methods, by providing a gene pen apparatus for the repetitive printing of arrays of molecules on solid or semi-solid supports.

BRIEF DESCRIPTION OF THE FIGURES

In FIG. 2A, a gene pen device containing a needle valve to control reagent flow is indicated. In FIG. 2B, a gene pen device containing a felt pen-type tip to control reagent flow is indicated. In FIG. 2C, a gene pen device wherein reagent flow and supply is maintained and controlled through capillary action is shown.

A soft porous plastic stamp pad, optionally containing a reagent reservoir, is shown. The stamp pad is saturated with the reagent used to facilitate immobilization of the desired test molecules.

SUMMARY OF THE INVENTION

The invention concerns gene pen apparatuses and methods for using gene pen apparatuses to print arrays on an array support. In detail, the invention provides a gene pen apparatus for DNA printing, comprising a reservoir containing an oligonucleotide, the reservoir being fluidly connected to a printing head, the printing head comprising a flow controlling means, especially a pin valve means or a felt tip means.

The invention also provides a gene pen apparatus for printing arrays on an array support containing an array-forming printhead, where the printhead contains a body and a printing face, the body having a multiplicity of bores therethrough, the printing face contains a multiplicity of fluid orifices, each of the fluid orifices being contiguous with at least one of the bores, the fluid orifices being spatially arranged in an array, and a multiplicity of reagent reservoirs, each of the reagent reservoirs being fluidly connected to at least one of the bores at an end, each of the reagent reservoirs being of sufficient volume to enable the printing of a multiplicity of the arrays.

The invention additionally concerns such apparatuses wherein the fluid connection is mediated by reagent-carrying tubes, most particularly wherein the printing face comprises the reagent-carrying tubes.

The invention also particularly concerns such apparatuses wherein the reagent-carrying tubes are themselves the reagent reservoirs.

The invention particularly concerns such gene pen apparatuses that contains at least 5, at least 10, at least 100, at least 1000, at least 10,000 and at least 10,000 fluid reservoirs.

The invention further is directed to such gene pen apparatuses where the printing face of the array-forming printhead is hydrophobic or hydrophilic.

The invention additionally concerns such array-forming printheads, additionally containing a mechanism to control the flow of reagent to the fluid orifices.

The invention particularly concerns such array-forming printheads additionally containing a pin valve positioned internally within the bore of each of the fluid orifices, the pin valve extending inwardly into the body of the printhead and extending outwardly beyond the printing face of the array-forming printhead, such that contacting the printing face of the printhead with an array support causes the pin valve to be pushed further into the orifice, opening the pin valve and allowing reagent fluid flow.

The invention further is directed to array-forming printheads additionally containing a felt tip positioned internally within the bore of each of the orifices, such that the felt tip and extends outwardly beyond the printing face of the array-forming printhead or a wicking member positioned internally within the bore of each of the orifices.

The invention additionally concerns gene pen apparatuses wherein the fluid connection is mediated by reagent-carrying tubes, the printing face comprises the reagent-carrying tubes, the printhead additionally comprising an outer retaining member, the reagent-carrying tubes being tightly packed within the outer retaining member, particularly wherein the outer retaining member is a tube of circular or rectangular cross-section.

The invention also particularly concerns such apparatuses wherein the reagent-carrying tubes are themselves the reagent reservoirs, particularly those apparatuses additionally comprising a wicking member positioned internally within the each of the reagent-carrying tubes or the fluid orifices.

The invention further is directed to gene pen apparatuses, wherein the flow controlling mechanism is a pressure differential between the fluid orifices and the reagent reservoirs.

The invention provides a method for printing an array of molecules on an array support, comprising the step of contacting at least one array-forming printhead of at least one gene pen apparatus with an array support, thereby transferring an amount of a multiplicity of reagent solutions to the array support so as to form an array on the support.

The invention also provides such methods, wherein the gene pen apparatus comprises a reservoir, the reservoir being fluidly connected to a printing head, the printing head comprising a flow controlling means.

The invention also provides such methods, wherein the gene pen apparatus comprises an array-forming printhead comprising a body, and a printing face, the body having a multiplicity of bores therethrough, the printing face comprising a multiplicity of fluid orifices, each of the fluid orifices being contiguous with at least one of the bores, the fluid orifices being spatially arranged in an array, and a multiplicity of reagent reservoirs, each of the reagent reservoirs being fluidly connected to at least one of the bores at an end, each of the reagent reservoirs being of sufficient volume to enable the printing of a multiplicity of the arrays.

The invention also relates to such methods, wherein a multiplicity of gene pens are contacted with the array support, particularly wherein the support is a solid or a semi-solid support.

The invention further is directed to such methods, wherein the array support is hydrophobic or hydrophilic.

The invention particularly concerns such methods, wherein the array support comprises array receptacles, the receptacles being hydrophilic and at least an area surrounding each of the array receptacles is hydrophobic or the receptacles being hydrophobic and at least an area surrounding each of the array receptacles is hydrophilic.

The invention further concerns such methods, wherein the hydrophobicity results from treatment of at least a portion of the array support with a hydrophobic silane and the hydrophilicity results from treatment of the array receptacles with a hydrophilic silane.

The invention also provides such methods, wherein the hydrophobicity results from treatment of at least a portion of the array support with hydrophobic silane and the hydrophilicity results from treatment of the array receptacles with protein, particularly wherein the protein is an antibody or streptavidin.

The invention provides methods for creating array receptacles on an array support comprising the steps of treating at least one surface of an array support with hydrophobic silane, and applying hydrophilic silane to the locations of the array receptacles.

The invention is particularly concerned with such methods, wherein the application of hydrophilic silane is accomplished with a self-inking stamp comprising a porous pad, the porous pad being impregnated with the hydrophilic silane, the porous pad comprising a printing surface, the surface comprising a multiplicity of printing tips, the tips being spatially arranged in an array.

The invention also provides methods for printing an array of molecules on an array support, comprising the steps of contacting at least one array-forming printhead of at least one gene pen apparatus with a transfer pad, such as a lithography transfer pad, thereby transfering a sufficient amount of a multiplicity of reagent solutions to the transfer pad and thereafter contacting the transfer pad, with an array support, thereby transferring a sufficient amount of the reagent solutions from the transfer pad to the array support so as to form an array on the array support.

The invention particularly concerns such methods, wherein the gene pen apparatus comprises n array-forming printhead comprising a body, and a printing face, the body having a multiplicity of bores therethrough, the printing face comprising a multiplicity of fluid orifices, each of the fluid orifices being contiguous with at least one of the bores, the fluid orifices being spatially arranged in an array, and a multiplicity of reagent reservoirs, each of the reagent reservoirs being fluidly connected to at least one of the bores at an end, each of the reagent reservoirs being of sufficient volume to enable the printing of a multiplicity of the arrays.

DETAILED DESCRIPTION OF THE INVENTION

I. Devices of the Present Invention

The particular devices of the present invention comprise a gene pen apparatus, suitable for printing arrays of molecules. Gene pen devices typically comprise a printing head, a reagent reservoir, and a mechanism to control reagent flow. The gene pen device may be composed of, or contain, any suitable material or combination of materials, such as nylon, polymer resins, polypropylene, glass, or metal. Portions of the gene pen device that are in direct communication with reagent fluid are preferably composed of material that is chemically resistant to the desired reagent fluid. Generally, easily machined materials such as stainless steel are used in the construction of the printing head. The gene pen device is most preferably composed principally of a soft temper stainless steel.

A. Printing Head

The printing head is composed of a body and a printing face. The printing face is that part of the gene pen apparatus that is contacted with the array support or transfer pad, thereby transferring an amount of one or more reagents to the support. In those embodiments wherein polar reagent fluids are used, the printing face is optionally treated so as to be hydrophobic. Conversely, in those embodiments wherein relatively nonpolar reagent fluids are used, the printing face is optionally treated so as to be hydrophilic. Such treatment facilitates reagent confinement and may be by any suitable means. The printing face contains one or more fluid orifices. The fluid orifices may be of any suitable shape, although round, square, elliptical, or quadrilateral is preferred. Similarly, the fluid orifices may be of any suitable size. In preferred embodiments, the fluid orifices are 1 mm in diameter or less, 0.1 mm to 1.0 mm in diameter, and more preferably 0.01 mm to 0.1 mm in diameter.

The fluid orifices may be produced by drilling holes through printing face and/or the body of the printing head. In accordance with the present invention, such drilling may be by any suitable means. Alternatively, the fluid orifices may be molded or cast into the printing face and/or body of the printing head. Suitable means for drilling fluid orifices include, for example, mechanical drilling via a drill bit, mill, laser drilling or other similar means. For most purposes of the present invention, the printing face of the printing head is preferably essentially planar. Consequently, following any drilling of fluid orifices, burrs and other machining debris and irregularities are preferably removed from the printing face. Removal of such machining debris and irregularities may be accomplished by a variety of suitable means including, but not limited to, polishing, grinding, acid bath, and solvent washing.

According to certain preferred embodiments of the present invention, one or more fluid orifices are the ends of the reagent-carrying tubes. In such embodiments, at least a portion of the body and the printing face of the printing head comprise reagent tubes themselves. In accordance with those embodiments comprising multiple reagent tubes, the reagent tubes may be tightly clustered together, interspersed only by a distance necessitated by the thickness of the side walls of the reagent tubes at the printing face. Alternatively, the reagent tubes may be positioned farther from one another, in which case the reagent tubes may be separated by spacer material, preferably interposed between the reagent tubes.

The reagent tube(s) are optionally held in place by an outer retaining member (FIG. 1). The outer retaining member may, according to certain preferred embodiments, define the overall shape of the array. Thus, the array may be of any shape. Preferred shapes, however, are circular and rectangular. The reagent tube(s) may optionally be affixed to one another, the optional spacer material, and/or the outer retaining member, by any suitable means. Examples of suitable means for affixing the position of the reagent tube(s) include, but are not limited to gluing, brazing, soldering, and/or welding. Generally, as noted above, it is desirable for the printing face to be essentially planer. The end of a reagent tube forming at least a portion of the printing face is therefore optionally machined, cleaned or polished so as to be essentially planar, co-planar with other fluid orifices of the printing face, preferably perpendicular to the reagent tube axis, and essentially free of burrs and other irregularities.

Figure 1A:
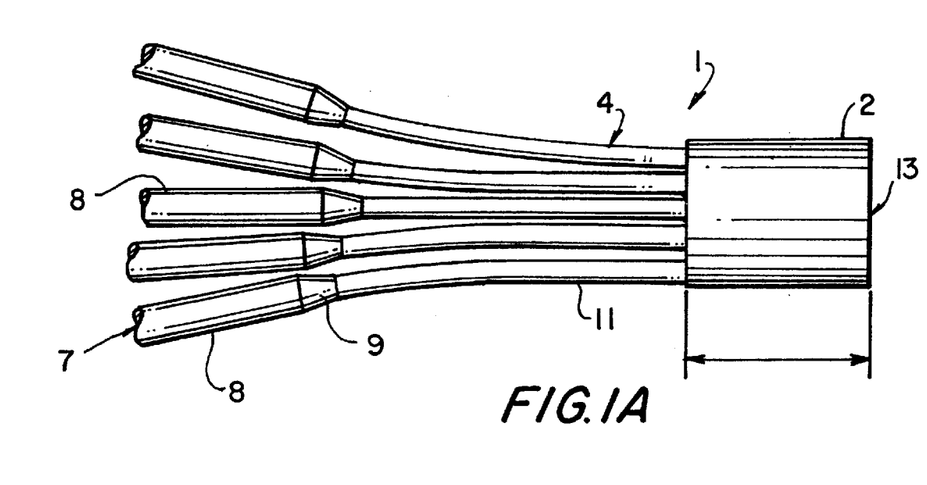
FIG. 1 provides a diagram of an embodiment of a gene pen apparatus of the present invention having multiple fluid orifices. The device, as depicted, is composed of a soft temper stainless steel alloy and contains multiple orifices.
Figure 1B:
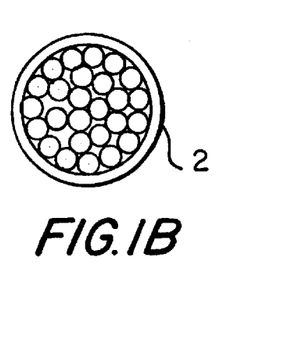
Figure 1C:
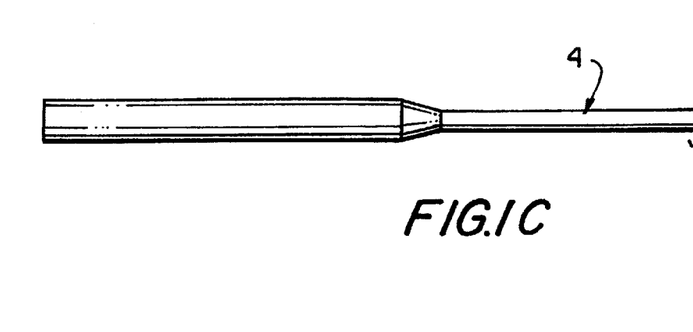
Figure 1D:
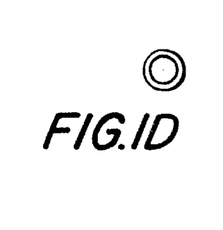
Figure 1E:
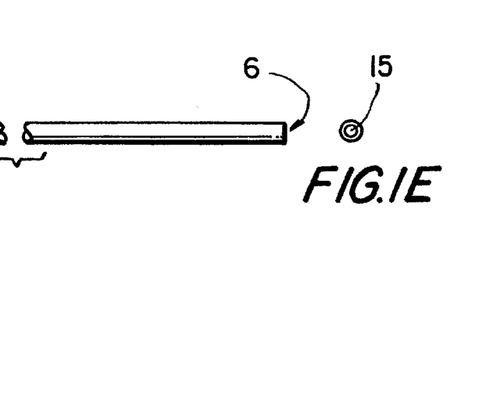
Figure 2A:
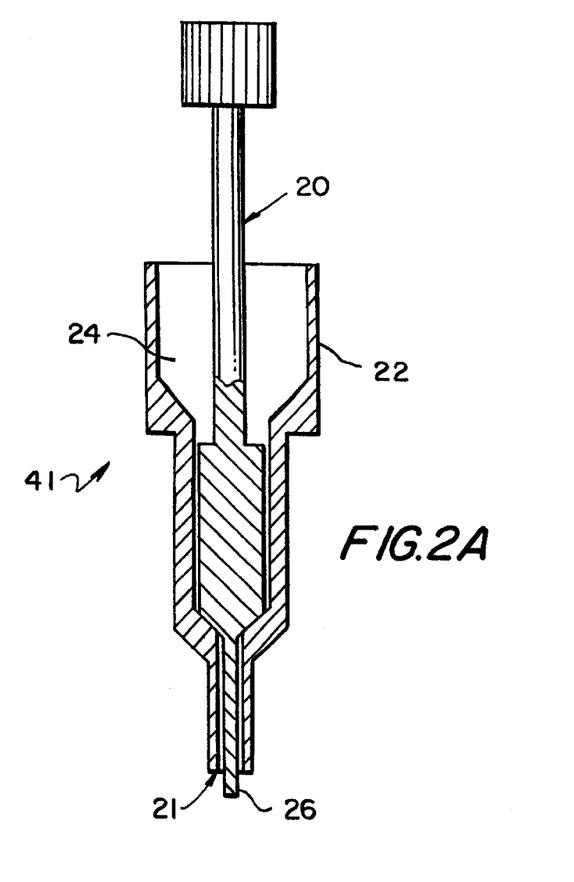
FIG. 2A–C provides a diagram of three embodiments of a gene pen apparatus of the present invention containing a single fluid orifice.
Figure 2B:
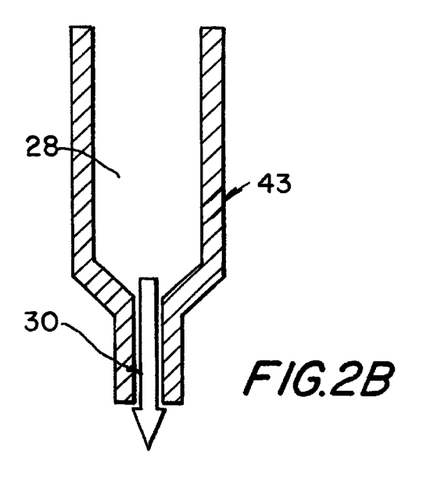
Figure 2C:
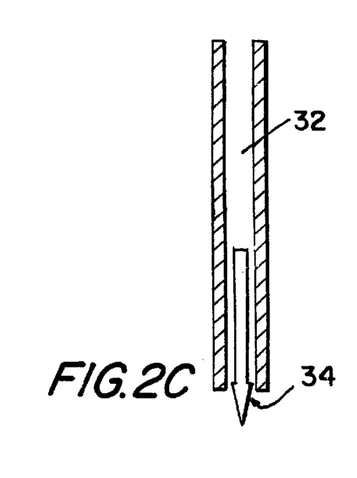
Figure 3:
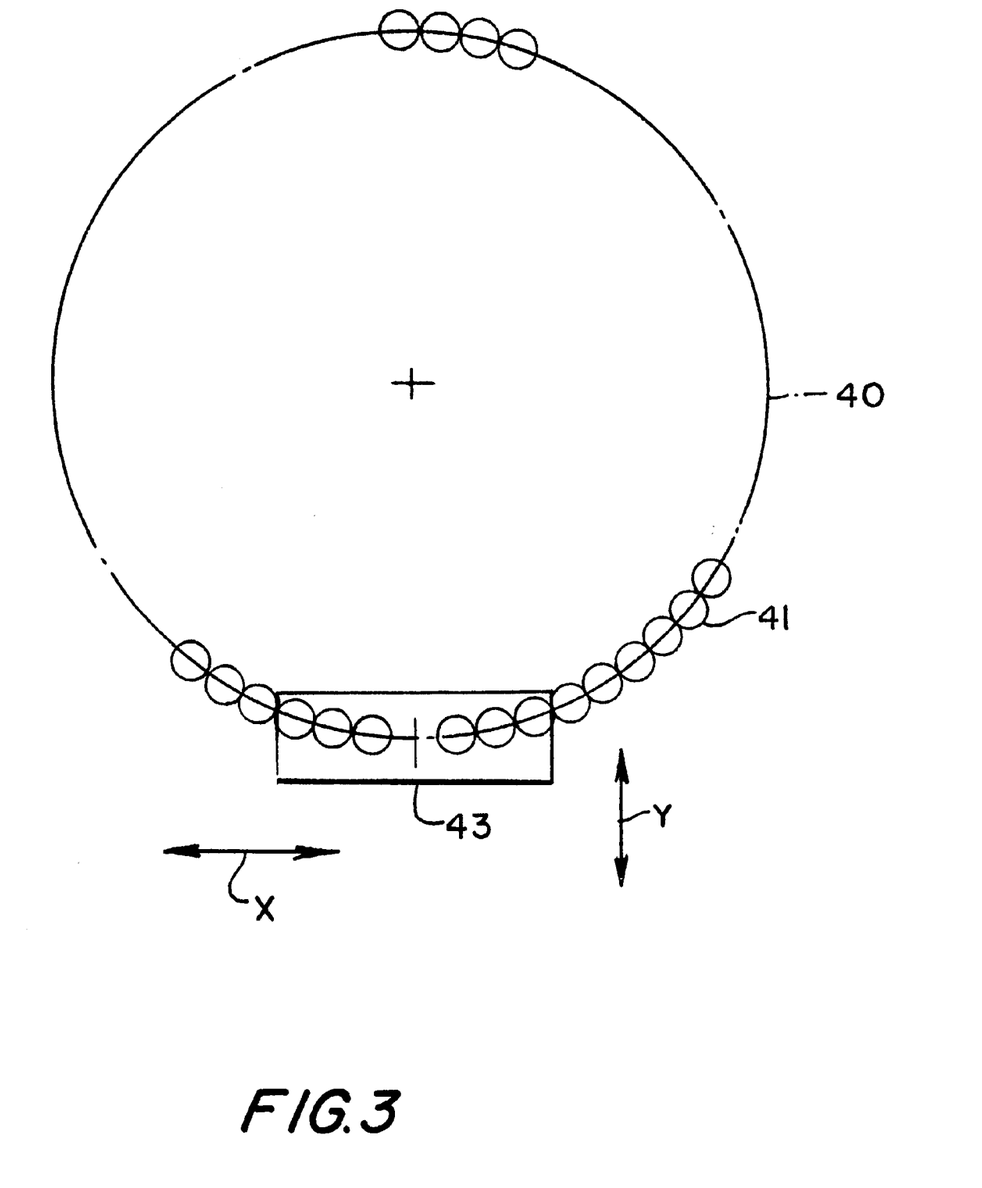
FIG. 3 provides a representation of one scheme for printing an array using multiple gene pen devices of the present invention. An indexing, rotating turntable is shown. Either the array support or the turntable or both may be moved transversely.

One advantage of the gene pen apparatus, is its ability to simultaneously print multiple different reagent molecules at discreet array positions. Thus, the printing head typically contains multiple fluid orifices and the desired array is preferably printed from a single gene pen device. Alternatively, as noted above, the array may be printed from multiple gene pen devices (FIGS. 2 and 3). Though the gene pen devices of the present invention may contain any number of fluid orifices, generally, the printing head of an individual gene pen device will contain about 5 to about 10 or more fluid orifices. According to certain embodiments of the present invention, the printing head contains about 10 to about 50 or more fluid orifices. In preferred embodiments, the printing head will contain at least about 50 or more to about 250 or more fluid orifices. Alternatively, printing heads containing at least about 250 to about 500, at least about 100 to about 1000, at least about 1000 to about 10,000 or more fluid orifices may be constructed.

B. Reagent Reservoir

Preferred gene pen devices of the present invention comprise one or more reagent reservoirs. In those embodiments wherein the printing head contains multiple fluid orifices, the gene pen devices of the present invention preferably contain multiple reagent reservoirs. Each reagent reservoir is connected, or connectable, to the printing head such that the reagent contained in the reservoir can be delivered to one or more orifices of the printing head. Generally, such fluid delivery is accomplished through one or more reagent-carrying tubes. Alternatively, the reagent reservoirs may be directly connected to the printing head or one or more fluid orifices. Preferably, each reagent reservoir is connected to a different fluid orifice of the printing head. In certain embodiments of the present invention, however, multiple reagent reservoirs may be connected to the same fluid orifice. Alternatively, an individual reagent reservoir may connected to multiple fluid orifices. In such embodiments, multiple array positions would receive the same test molecule or individual array positions could receive multiple species of molecules. Such configurations are useful, for example, for quality control and other purposes.

Each reagent reservoir of the gene pen device preferably provides sufficient reagent to the fluid orifice or orifices to which it is connected, so as to facilitate the printing of multiple arrays. Each reservoir may be of any suitable shape and composed of any material suitable for containing the reagent held within. Preferred shapes for individual reagent reservoirs include, but are not limited to that of a tube, vial, or flask. Similarly, each reagent-carrying tube may be of any suitable material or dimension for containing the reagent being carried from each reagent reservoir its respective fluid orifice(s) of the printing head. The dimensions of the end of each reagent tube connected to the printing head are preferably sufficiently small so as to allow the desired number of reagent tubes to be positioned to the spacing dimensions of the fluid orifices of the printing head. As the quantity of reagent used in each printing operation is small, the size of the reagent reservoir is relatively unimportant for the purposes of the present invention. Thus, according to certain embodiments of the present invention, the reagent-carrying tube may itself be the reagent reservoir. Preferably, the reagent reservoir will be of sufficient size to supply reagent for at least 5, more preferably at least 100 and most highly preferably at least 1000 printing operations.

According to certain preferred embodiments, each fluid orifice of the printing head is in fluid communication with a reagent reservoir. However, it is not essential for the purposes of the present invention for all fluid orifices to be connected to one or more reagent reservoirs. For example, according to certain embodiments of the present invention, it may be desirable for individual fluid orifices to not be connected to a reservoir and therefore require adding reagent with each iteration of the array-printing operation.

C. Mechanisms to Control Reagent Flow

Certain embodiments of the present invention additionally contain one or more mechanisms to control the rate of reagent flow to or through the fluid orifices. Such control preferably facilitates reagent confinement, metering, and parallelism. Control may be either active or passive or both, by any suitable means. Typically, the devices of the present invention preferably utilize at least one mechanism of passive flow control to control reagent supply in the production of the desired array. Furthermore, certain embodiments of the present invention, aspects of both active and passive control of reagent flow are incorporated in a single gene pen device. Active control may, for example, be through the interposition of a valve or the application of a pressure differential between the reagent reservoir and the fluid orifice. Passive control may be through a variety of suitable means as well. These include, but are not limited to, viscosity, capillary action, surface tension, hydrophobic interactions, hydrophilic interactions, and gravity. In addition, certain embodiments of the present invention may utilize passive valves or switches.

A needle valve is an example of a preferred suitable mechanism for passive control of reagent flow (FIG. 2a). In certain preferred embodiments of the present invention, each fluid orifice preferably contains the pin of a needle valve positioned internally within the bore of the fluid orifice. The pin typically extends at least partially into the body of the printing head, with the tip of the pin preferably extending a suitable distance beyond the printing face, such that an array support brought into juxtaposition with the printing face is first brought into contact with the extended tip of the pin. Contact between the printing face and the array support therefore preferably causes the pin to be pushed inwardly toward the body of the printing head, thereby opening the needle valve and allowing reagent flow. In such preferred embodiments, the valve is normally closed when the printing face is not in contact with the desired array support.

Alternatively, or in combination with another flow controlling mechanism, reagent flow may be passively controlled through the use of wicking member positioned in the path of reagent fluid flow. The wicking member may be composed of any suitable substance. Examples of suitable preferred wicking substances include, but are not limited to paper, glass wool, acrylic, polyester, nylon, wool, cellulose, and polyethylene. The wicking material is preferably chosen so as to be resistant to dissolution in the desired reagent fluid. The wicking member may be suitably positioned in the reagent reservoir, the reagent carrying tube, and/or the bore passing through the printing head. The wicking member may also be suitably positioned within the bore of one or more fluid orifices. According to such embodiments, the wicking member preferably comprises a pen tip, such as a felt tip, that preferably extends a suitable distance outward beyond the printing face of the printing head, such that an array support brought into juxtaposition with the printing face is brought into contact with the extended pen tip (FIGS. 2b and 2c).

As noted above, application of a pressure differential between the reagent reservoir and the fluid orifice is an example of an active flow control mechanism. According to certain embodiments of the present invention, particularly in those embodiments wherein the reagent reservoirs are substantially composed of reagent-carrying tubes, reagent flow to the fluid orifices may be suitably controlled by altering the atmospheric pressure applied to the open ends of the reagent reservoirs.

II. Array Supports the Present Invention

The devices of the present invention are preferably used to print arrays of molecules on a suitable array support. Suitable array supports include those to which organic molecules, such protein and nucleic acid, may be covalently or non-covalently attached by any means known in the art. Suitable array supports may be solid or semi-solid. In those embodiments wherein the support is semi-solid, the semi-solid support preferably comprises a layer affixed to a solid support. Suitable solid supports for the present invention therefore include, but are not limited to substrates composed of silicon, glass, paper, plastic (such as polystyrene, nylon, and polypropylene), and cellulose. Examples of suitable semi-solid supports for the purposes of the present invention include, but are not limited to agar, agarose, polyacrylamide, and suitable combinations thereof. Suitable semi-solid supports preferably allow the test molecules of the present invention to diffuse a limited distance into the support upon printing of the array. Following printing of the array, the test molecules are preferably fixed within such a semi-solid support by suitable means such as chemical cross-linking, UV cross-linking or drying.

For the purposes of the present invention, array supports are preferably formed into substantially planer surfaces, such as plates, slides, sheets, membranes, or chips. Alternatively, array supports may be formed into other shapes, such as wells (as in 96-well dishes), fibers, dishes, and beads.

A. Treatment of the Array Support

According to certain embodiments of the present invention, the array support is suitably treated, coated, or derivatized, so as to facilitate the immobilization of the molecules that are to be formed into an array. Such treatment also preferably facilitates reagent confinement to the desired array positions (array receptacles). Suitable treatment may include the entire array support, an entire surface of the array support, the locations on the array support of the array receptacles, the area surrounding the array receptacles, or a combination thereof. In certain embodiments, however, certain of the aforementioned regions are left untreated. Generally, in performing the methods of the present invention, the positions of the array receptacles and the area surrounding the array receptacles receive different treatments (or non-treatment), coatings, or derivatizations. This differential treatment preferably facilitates confinement of individual species of immobilized test molecules to their respective array receptacles.

The treatment, coating, or derivatization of the array support is generally performed prior to the addition of the molecules to the array support. According to certain methods of the present invention, however, the treatment, coating, or derivatization is performed contemporaneous with or subsequent to the addition of the molecules to be formed into an array. Low salt immobilization of nucleic acid is an example of a treatment generally performed contemporaneous with the addition of the molecules to the array support. In contrast, U.V. cross-linking is an example of a treatment generally performed subsequent to the addition of the molecules to the array support.

Preferred treatments, coatings, or derivatizations suitable to the methods of the present invention include, but are not restricted to poly-L-Lys, streptavidin, antibodies, polypeptides, silane derivatives, low salt, plasma, photo-irradiation, or acid. Choice of treatment, coating or derivatization is preferably guided by the nature of the array support and the molecules that are to be immobilized in an array. A variety of suitable attachment chemistries are well known in the art.

According to those embodiments wherein the reagent solution is polar, the positions of the array receptacles are preferably hydrophilic or treated so as to be hydrophilic. To facilitate reagent confinement in such embodiments, the area surrounding each array receptacle is preferably hydrophobic or treated so as to be hydrophobic. Conversely, in those embodiments wherein the reagent solution is relatively non-polar, the positions of the array receptacles are preferably hydrophobic or treated so as to be hydrophobic. Similarly, in such embodiments, the area surrounding each array receptacle is preferably hydrophilic or treated so as to be hydrophilic to facilitate reagent confinement. In certain embodiments of the present invention, however, both the positions of the array receptacles and the area surrounding the array receptacles are treated so as to both be hydrophobic or both be hydrophobic. In certain embodiments of the present invention, an entire surface of the array support is treated so as to be hydrophilic or hydrophobic. Alternatively, the positions of the array receptacles and the area surrounding the array receptacles may first be treated so as to be generally hydrophobic and the area surrounding the positions of the array receptacles may subsequently be treated so as to be hydrophilic.

Figure 4A:
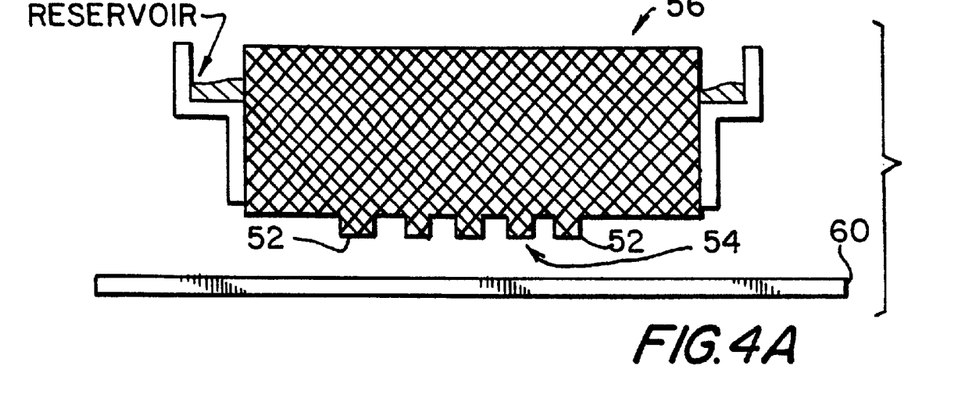
FIG. 4 provides a diagram of an example of two embodiments of a stamp pad embodiment of the present invention for printing array receptacles on an array support.
Figure 4B:
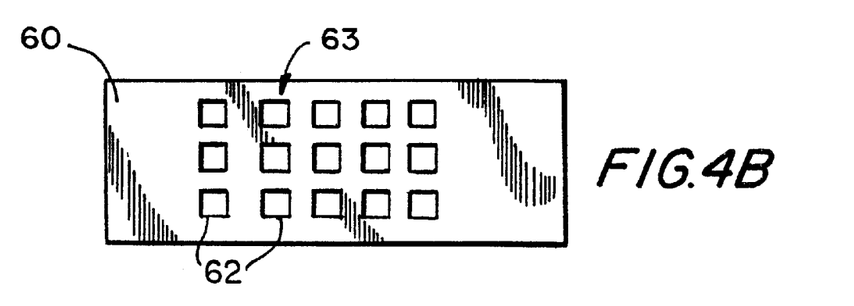
Figure 4C:
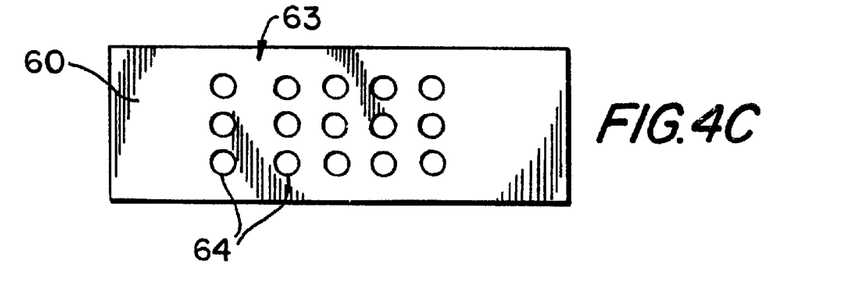

According to certain embodiments of the present invention, array receptacles are created on the array support through the use of a suitable stamp or stamp pad (FIG. 4). A self inking-type soft porous plastic stamp pad is an example of a suitable stamp pad. The stamp is most preferably formed into a pattern suitable for printing the desired array on the array support. The stamp pad is preferably formed so as to contain a multiplicity of printing tips on the printing face of the stamp. Alternatively, the stamp pad may be formed so as to imprint an area surrounding, but not including, the array receptacles. Preferably, the stamp is formed in desired pattern by photoengraving. The stamp pad may, however, be molded or formed into the desired pattern by any suitable method.

In embodiments wherein a stamp is used to print array receptacles on the array support, the stamp is preferably impregnated with a suitable material, dependant on the desired attachment chemistry, so as to facilitate the binding of the desired molecules to the array support. Examples of suitable material include, but are not limited to poly-L-Lys, streptavadin, antibodies, protein, hydrophilic or hydrophobic silane, low salt, or acid. According to a highly preferred embodiment, the array support is treated so as to be generally hydrophobic. A stamp pad, impregnated with a hydrophilic silane derivative, and formed so as to provide a multiplicity of printing tips spatially arranged in an array, is subsequently impressed upon the surface of the array support, thereby printing array receptacles on the array support.

III. Direct Printing Methods of the Present Invention

The methods of the present invention preferably comprise the use of the devices of the present invention to print an array of molecules on an array support of the present invention.

The devices of the present invention are useful for the production of arrays composed of any desired test molecules, though the production of arrays of organic molecules are preferred. Particular preferred uses for the devices of the present invention include the production of arrays of organic molecules including nucleic acid, and polypeptides. The devices of the present invention are most preferably used for the production of arrays of DNA, particularly oligonucleotides.

Generally, in performing the direct printing methods of the present invention, one or more devices of the present invention are contacted at least once with one array support of the present invention, thereby transferring a desired amount of one or more desired test reagents onto an array support.

In those embodiments wherein the gene pen device contains a multiplicity of fluid orifices, printing the array on an array support is preferably accomplished with a single contacting of the gene pen device to the array support, preferably at locations of array receptacles. As increased array printing speed is considered desirable for the purposes of the present invention, such embodiments are particularly preferred. Such methods additionally facilitate the repetitive printing of a multiplicity of substantially identical arrays. Accordingly, in certain embodiments of such methods, repetative printing operations are preferably automated by suitable means, such as robotics. In embodiments where the desired array complexity is greater than the number of fluid orifices in the printing head, multiple gene pen devices may be used to print an individual array. Alternatively, a single gene pen device contacted with a single array support multiple times. Additionally, according to certain preferred methods of the present invention, multiple arrays are printed upon a single array support.

In those embodiments wherein the gene pen device contains a single fluid orifice, printing each position of the array on an array support is preferably accomplished with a single contacting of a gene pen device to the array support, preferably at the location of an array receptacle. The array is preferably printed with a series of different gene pen devices, where the different devices preferably contain different test reagents. In certain embodiments of such methods, however, it is desirable for certain of the gene pen devices to contain identical test reagents. Preferably, in performing those methods where individual gene pen devices each contain a single fluid orifice, each array position is printed individually. In such methods, an automated device, such as an indexing turntable (FIG. 3) or a robotic arm is preferably used to correctly place each reagent at its desired array position on the array support. According to some such methods, the array support may additionally translate horizontally in the x and/or y directions, so as to facilitate correct reagent placement.

Typically, in performing any of the printing methods of the present invention, the array supports are preferably treated, coated, or derivatized as described above, so as to facilitate immobilization of the desired test molecules. Also typically, this treatment is prior to the contacting of the gene pen device to the array support. Generally, such treatments of the array support result in the formation of array receptacles. Preferred treatments additionally facilitate confinement of each desired reagent to its respective desired array receptacle.

IV. Indirect Printing Methods of the Present Invention

Figure 5:
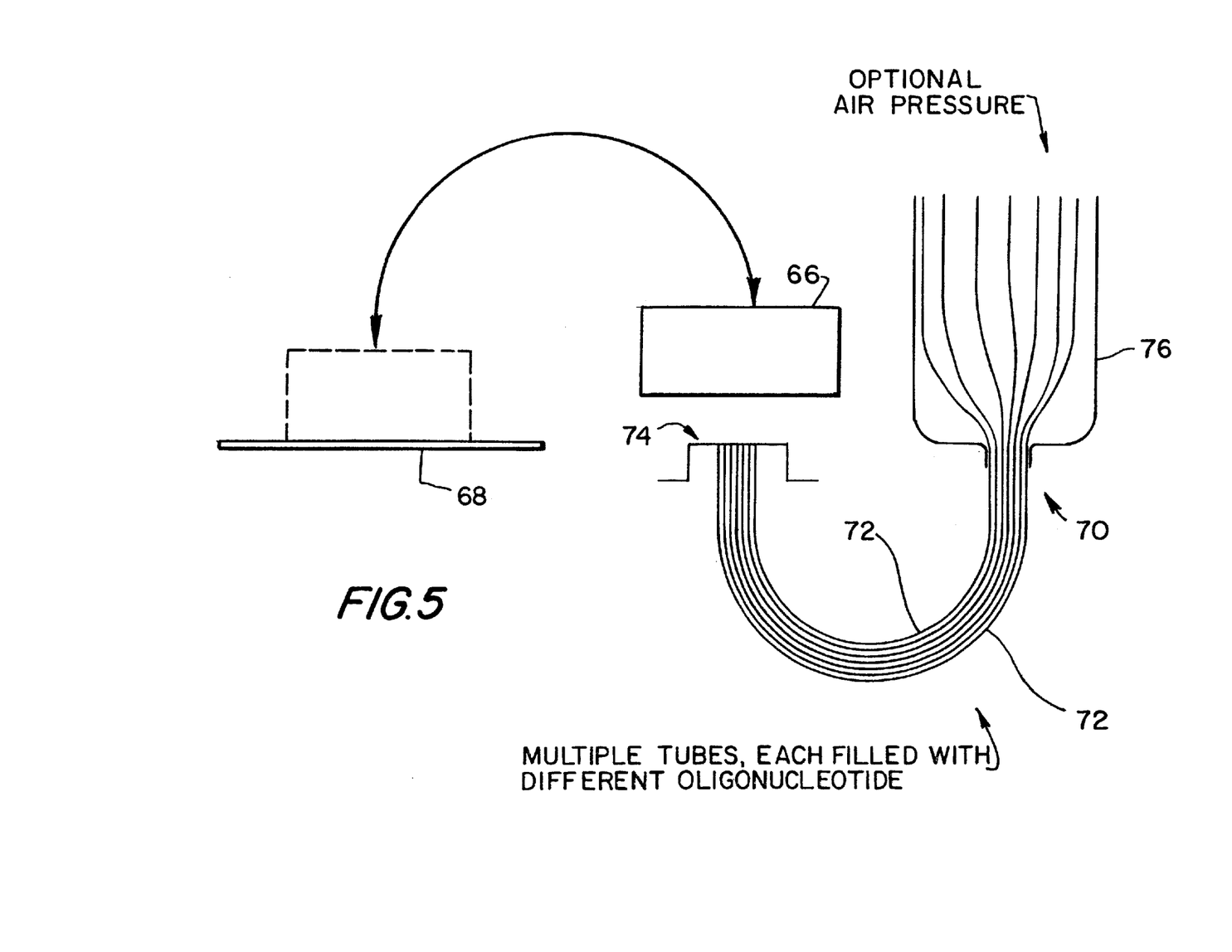
FIG. 5 provides a representation of a method of the present invention for indirectly printing an array on an array support using an embodiment of a gene pen device containing multiple fluid orifices. Reagent transfer is optionally facilitated through the application of an atmospheric pressure differential between the reagent reservoirs and the fluid orifices at the printing face of the gene pen device. The array or desired test molecules is first printed on a transfer pad. A rubber lithographic pad is indicated. The array is subsequently transferred from the transfer pad to the array support through direct contact.

According to certain alternate embodiments of the present invention, the array is indirectly printed on the array support. In such embodiments, the array is first printed on a suitable transfer pad (FIG. 5). The array may be directly printed on the transfer pad in accordance with any suitable direct printing method of the present invention. Thereafter, the transfer pad containing the arrayed molecules is preferably contacted with the array support, thereby transferring the desired array of test molecules to the array support. A soft rubber lithography pad is an example of a preferred suitable transfer pad.

Such embodiments may be used, for example, when it is desired to provide a mirror image of the array that would be printed by the direct printing method of the present invention, when used alone. Alternatively, such methods provide the advantage of correcting for a certain lack of planarity to the printing face, printing tips, and/or felt tips projecting from the printing face. Thus, certain embodiments of the such indirect printing methods provide improved evenness of reagent transfer, facilitating the printing of repetative copies of substantially identical arrays.

Having now generally described the invention, the same may be more readily understood through the following reference to the following examples, which are provided by way of illustration and are not intended to be limiting of the present invention unless specified.

EXAMPLES

Example I

Design of a Gene Pen Device

A gene pen device is assembled from a multiplicity of individual tubular members, as shown in FIG. 1. Each member is composed of a soft temper stainless steel alloy. Each member has a reagent reservoir at one end, which is open at one end and gradually tapered at its other end. The tapered end is connected to a capillary tube, which serves as the reagent-carrying tube. The reagent reservoir is 1.0±0.06 inches in length, with an inner diameter of 0.09 inches. The capillary tube is, as noted, connected at one end to the reagent reservoir. The other end is polished burr-free and square with the capillary tube axis. The capillary tube itself is approximately 3.00±0.12 inches in length, with an internal diameter of 0.035 inches and a wall thickness of approximately 0.013±0.0015 inches.

A number of the individual tubular members are assembled together to form the gene pen device. At the printing end, the capillary tubes (reagent-carrying tubes) are tightly packed into an outer retaining tubular member. An outer retaining member of approximately 1.00 inches in length and approximately 0.02 inches in thickness is used. The polished end of each capillary tube is positioned within the outer retaining member, so as to be flush with one end of the retaining member. Thus, the printing head of the gene pen device is composed of tightly packed reagent carrying tubes. Consequently, the ends of the capillary tubes that are flush with the end of the retaining member and the flush end of the outer retaining member becomes the printing face of the printing head and the end of each capillary tube provides a fluid orifice. A small felt tip is optionally placed within each fluid orifice.

Example II

Printing with Gene Pen Device Containing a Pin Valve

FIG. 2A depicts a gene pen device containing a single reagent reservoir, a single fluid orifice, and a pin valve to control reagent flow. A multiplicity of such devices are placed in a rotating turntable, which is positioned over an indexing table that is translatable in both the x and y directions, as depicted in FIG. 3. 61 devices are placed in an 8 inch diameter turntable. Each device has an outer diameter of 0.350 inches, spaced 0.375 inches apart.

During each iteration, the turntable holding the gene pen devices and the table holding the array support are each indexed one position, positioning a new gene pen device over a new array receptacle on the glass slide being used as an array support. The gene pen is then lowered to contact the glass slide. Contact between the printing face and the glass slide causes the pin valve of the gene pen to be pushed inwardly into the body of the device, allowing a small amount of reagent to flow out onto the glass slide at the position of an array receptacle. The device is then raised back up, closing the pin valve. The rotating turntable and the indexing array support table are again indexed one position, the next gene pen device is contacted with the array support, and the process is repeated until the desired array is printed.

Example III

Robotic Printing with Gene Pen Device Containing a Pin Valve

Figure 6:
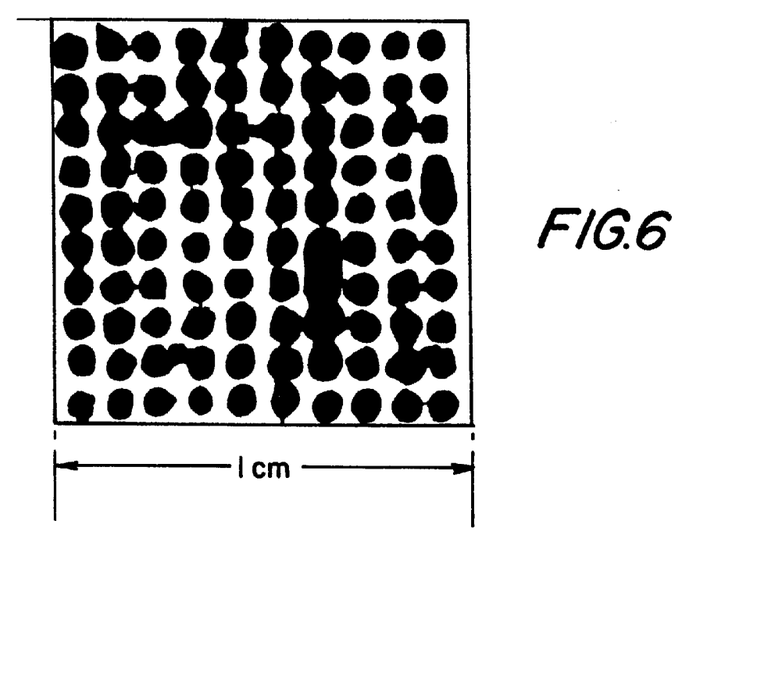
FIG. 6 provides a fluorescence image of an array printed with a valve pin type gene pen device.

A Hamilton robot is used to print an oligonucleotide array using a single-reservoir gene pen device, similar to the device depicted in FIG. 2A. In this particular example, a single oligonucleotide species is printed at all array positions at an array density of 100 oligonucleotides/cm$^2$ (FIG. 6).

During each iteration of the printing operation, the Hamilton Robot positions the gene pen device over an array receptacle on the glass slide being used as an array support. The gene pen is then lowered to contact the glass slide. Contact between the printing face and the glass slide causes the pin valve of the gene pen to be pushed inwardly into the body of the device, allowing a small amount of reagent to flow out onto the glass slide at the position of an array receptacle. The device is then raised back up, closing the pin valve. The arm of the Hamilton Robot repositions over the next array receptacle and the gene pen device is again contacted with the array support. The process is repeated until the desired array is printed.

Example IV

Robotic Printing with Gene Pen Device Containing a Porous Wicking Tip

Figure 7:
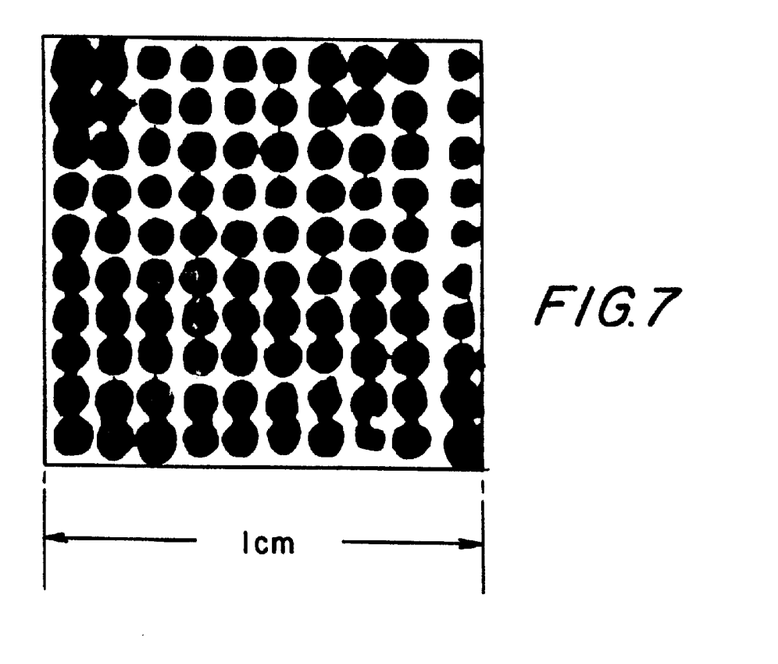
FIG. 7 provides a fluorescence image of an array printed with a porous wicking tip gene pen device.

A Hamilton Robot is used to print an oligonucleotide array using a single-reservoir gene pen device, similar to the device depicted in FIG. 2B. In this particular example, a single oligonucleotide species is printed at all array positions at an array density of 100 oligonucleotides/cm$^2$ (FIG. 7).

During each iteration of the printing operation, the Hamilton Robot positions the gene pen device over an array receptacle on the glass slide being used as an array support. The gene pen is then lowered to contact the glass slide. Contact between the porous wicking tip and the glass slide causes a small amount of reagent to be deposited onto the glass slide at the position of an array receptacle. The device is then raised back up. The arm of the Hamilton Robot repositions over the next array receptacle and the gene pen device is again contacted with the array support. The process is repeated until the desired array is printed.

Example V

Printing Array Receptacles on an Array Support

An array pattern is photoengraved onto the printing surface of a soft porous plastic stamp pad, using standard methods. The stamp pad is then saturated with a dilute solution of a hydrophilic functionalized silane (FIG. 4).

A glass slide is used as an array support. The glass slide is first thoroughly cleaned. Next, the glass slide is treated with hydrophobic silane. The slide is again thoroughly cleaned. The saturated stamp pad is then contacted with the surface of the slide, imprinting an array pattern of hydrophilic functionalized silane onto the glass slide, creating array receptacles. The slide is again thoroughly washed before use as an array support.

Example VI

Indirect Printing with a Gene Pen Device

A gene pen device is assembled using bundled capillary tubes. The tubes are held together at the printing head end, as described in Example I. In this example, the capillary tubes themselves form the reagent reservoirs. At the non-printing face end of the capillary tubes, the tubes are held in a bell jar, suitably sealed to allow the application of air pressure to force reagent fluid to flow out the fluid orifices of the printing face.

Moderate air pressure is applied, and a soft rubber lithography transfer pad is placed in contact with the printing face, transferring a small amount of each reagent solution to the transfer pad. The transfer pad is then immediately contacted with a pre-treated glass slide, transferring the arrayed test reagents from the transfer pad to the pre-treated glass slide.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A gene pen apparatus for delivering arrays of oligonucleotides on an array support comprising:
   (A) an array-forming printhead, said printhead comprising a body, a printing face, and a flow controlling means, said body having, a multiplicity of bores therethrough, said printing face comprising a multiplicity of fluid orifices, each of said fluid orifices being contiguous with at least one of said bores, said fluid orifices being spatially arranged in an array, and said flow controlling means is either a pin valve means or wicking member means, wherein the flow controlling means is located at the fluid orifices; and
   (B) a multiplicity of reagent reservoirs, each of said reagent reservoirs being fluidly connected to at least one of said bores at an end, each of said reagent reservoir being of sufficient volume to enable the printing of a multiplicity of said arrays.

2. The gene pen apparatus of claim 1, comprising at least 5 fluid reservoirs.

3. The gene pen apparatus of claim 1, comprising at least 10 fluid reservoirs.

4. The gene pen apparatus of claim 1, comprising at least 100 fluid reservoirs.

5. The gene pen apparatus of claim 1, comprising at least 1000 fluid reservoirs.

6. The gene pen apparatus of claim 1, comprising at least 10,000 fluid reservoirs.

7. The gene pen apparatus of claim 1, comprising at least 100,000 fluid reservoirs.

8. The array-forming printhead of claim 1, wherein said printing face is hydrophobic.

9. The array-forming printhead of claim 1, wherein said printing face is hydrophilic.

10. The array-forming printhead of claim 1, wherein the flow controlling means is a pin valve positioned internally within the bore of each of said fluid orifices, said pin valve extending inwardly into the body of said printhead and extending outwardly beyond the printing face of said array-forming printhead, such that contacting said printing face of said printhead with an array support causes said pin valve to be pushed further into said orifice, opening said pin valve and allowing reagent fluid flow.

11. The array-forming printhead of claim 9, wherein the flow controlling means is a pin valve positioned internally within the bore of each of said fluid orifices, said pin valve extending inwardly into the body of said printhead and extending outwardly beyond the printing face of said array-forming printhead, such that contacting said printing face of said printhead with an array support causes said pin valve to be pushed further into said orifice, opening said pin valve and allowing reagent fluid flow.

12. The array-forming printhead of claim 1, wherein the flow controlling means is a wicking means, said wicking member means comprising a felt tip positioned internally within the bore of each of said orifices, such that said felt tip extends outwardly beyond the printing face of said array-forming printhead.

13. The array-forming printhead of claim 9, wherein the flow controlling means is a wicking means, said wicking member means comprising a felt tip positioned internally within the bore of each of said orifices, such that said felt tip extends outwardly beyond the printing face of said array-forming printhead.

14. The array-forming printhead of claim 1, additionally comprising a wicking member positioned internally within the bore of each of said orifices.

15. The gene pen apparatus of claim 1, wherein said fluid connection is mediated by reagent-carrying tubes.

16. The gene pen apparatus of claim 15, wherein said printing face comprises said reagent-carrying tubes.

17. The gene pen apparatus of claim 15, wherein said reagent-carrying tubes are said reagent reservoirs.

18. The array-forming printhead of claim 16, additionally comprising an outer retaining member, said reagent-carrying tubes being tightly packed within said outer retaining member.

19. The array-forming printhead of claim 18, wherein said outer retaining member is a tube of circular cross-section.

20. The array-forming printhead of claim 18, wherein said outer retaining member is a tube of rectangular cross-section.

21. The gene pen apparatus of claim 16, additionally comprising a wicking member positioned internally within the each of said reagent-carrying tubes.

22. The gene pen apparatus of claim 16, additionally comprising a wicking member positioned internally within each of said reagent reservoirs.

23. The gene pen apparatus of claim 16, additionally comprising a wicking member positioned internally within the each of said fluid orifices.

24. A method for printing an array of molecules on an array support, comprising the step of contacting at least one array-forming printhead of at least one pen apparatus, with an array support, thereby transferring an amount of a multiplicity of reagent solutions to the array support so as to form an array on said support, said gene pen apparatus comprising:

(A) an array-forming printhead, said printhead comprising a body, and a printing face, said body having a multiplicity of bores therethrough, said printing face comprising a multiplicity of fluid orifices, each of said fluid orifices being contiguous with at least one of said bores, said fluid orifices being spatially arranged in an array, and (B) a multiplicity of reagent reservoirs, each of said reagent reservoirs having a reagent flow controlling means, said reagent flow controlling means being comprised of either a pin valve means or a wicking means, said reagent reservoirs being fluidly connected to at least one of said bores at an end, each of said reagent reservoirs being of sufficient volume to enable the printing of a multiplicity of said arrays.

25. The method of claim 24, wherein a multiplicity of gene pens are contacted with the array support.

26. The method of claim 24, wherein said array support is a solid support.

27. The method of claim 24, wherein said array support is a semi-solid support.

28. The method of claim 24, wherein said array support is hydrophobic.

29. The method of claim 24, wherein said array support is hydrophilic.

30. The method of claim 24, wherein said array support comprises array receptacles, said receptacles being hydrophilic and at least an area surrounding each of said array receptacles is hydrophobic.

31. The method of claim 24, wherein said array support comprises array receptacles, said receptacles being hydrophobic and at least an area surrounding each of said array receptacles is hydrophilic.

32. The method of claim 30, wherein said hydrophobicity results from treatment of at least a portion of said array support with a hydrophobic silane and said hydrophilicity results from treatment of said array receptacles with a hydrophilic silane.

33. The method of claim 31, wherein said hydrophobicity results from treatment of at least a portion of said array support with a hydrophobic silane and said hydrophilicity results from treatment of said array receptacles with a hydrophilic silane.

34. The method of claim 31, wherein said hydrophobicity results from treatment of at least a portion of said array support with hydrophobic silane and said hydrophilicity results from treatment of said array receptacles with protein.

35. The method of claim 34, wherein said protein is an antibody.

36. The method of claim 34, wherein said protein is streptavidin.

37. A method for printing an array of molecules on an array support, comprising the steps of:

(A) contacting at least one array-forming printhead of at least one gene pen apparatus, with a transfer pad, thereby transferring a sufficient amount of a multiplicity of reagent solutions to said transfer pad, said gene pen apparatus comprising a printing head and a reagent reservoirs, said reagent reservoir having a reagent flow controlling means; and (B) contacting said transfer pad with an array support, thereby transferring a sufficient amount of said reagent solutions from said transfer pad to the array support so as to form an array on said array support.

38. The method of claim 37, wherein said gene pen apparatus comprises:

(A) an array-forming printhead, said printhead comprising a body, and a printing face, said body having a multiplicity of bores therethrough, said printing face comprising a multiplicity of fluid orifices, each of said fluid orifices being contiguous with at least one of said bores, said fluid orifices being spatially arranged in an array, and (B) a multiplicity of reagent reservoirs, each of said reagent reservoirs being fluidly connected to at least one of said bores at an end, each of said reagent reservoirs being of sufficient volume to enable the printing of a multiplicity of said arrays.

39. The method of claim 38, wherein said transfer pad of claim 37 is a lithography transfer pad.

40. The method of claim 24, wherein said printhead has at least one fluid orifices per $cm^2$.

41. The method of claim 24, wherein said printhead has at least ten fluid orifices per $cm^2$.

42. The method of claim 24, wherein said printhead has at least one hundred fluid orifices per $cm^2$.

43. The method of claim 24, wherein said printhead has at least one thousand fluid orifices per $cm^2$.

* * * * *